United States Patent
Messaoudi et al.

(10) Patent No.: US 12,004,515 B2
(45) Date of Patent: Jun. 11, 2024

(54) USE OF A GRAPE EXTRACT AS A VIRUCIDE AGAINST VIRUSES OF THE CORONAVIRUS FAMILY

(71) Applicant: BERKEM DEVELOPPEMENT, Blanquefort (FR)

(72) Inventors: Daouïa Messaoudi, Saint-Priest (FR); Olivier Fahy, Bordeaux (FR); Jean-Louis Peron, Lamonzie Saint Martin (FR); Jean Nkiliza, Saint Antoine de Breuilh (FR)

(73) Assignee: Berkem Developpement, Blanquefort (FR)

( * ) Notice: Subject to any disclaimer, the term of this patent is extended or adjusted under 35 U.S.C. 154(b) by 0 days.

(21) Appl. No.: 17/684,476

(22) Filed: Mar. 2, 2022

(65) Prior Publication Data

US 2022/0279797 A1     Sep. 8, 2022

(30) Foreign Application Priority Data

Mar. 3, 2021   (FR) ...................................... 2102076

(51) Int. Cl.
| | | |
|---|---|---|
| *A61K 36/00* | (2006.01) | |
| *A01N 65/08* | (2009.01) | |
| *A01P 1/00* | (2006.01) | |
| *A61K 8/9789* | (2017.01) | |
| *A61Q 17/00* | (2006.01) | |

(52) U.S. Cl.
CPC ................ *A01N 65/08* (2013.01); *A01P 1/00* (2021.08); *A61K 8/9789* (2017.08); *A61Q 17/005* (2013.01)

(58) Field of Classification Search
CPC ................................ A01P 1/00; A61Q 17/005
See application file for complete search history.

(56) References Cited

U.S. PATENT DOCUMENTS

2018/0104194 A1     4/2018   Johnson

FOREIGN PATENT DOCUMENTS

| CN | 111184799 A | | 5/2020 |
|---|---|---|---|
| JP | 2005314316 A | * | 11/2005 |
| JP | 2005314316 A | | 11/2005 |
| JP | 6836229 B2 | | 2/2021 |
| WO | 2018191409 A1 | | 10/2018 |

OTHER PUBLICATIONS

Snehal et al, Antiviral effects of grape seed extract against feline calicivirus, murine norovirus, and hepatitis A virus in model food systems and under gastric conditions. Food microbiology, (Dec. 2015) vol. 52, pp. 1-10 (Year: 2015).*
Li, Effect of grape seed extract on human norovirus GII.4 and murine norovirus 1 in viral suspensions, on stainless steel discs, and in lettuce wash water. Applied and environmental microbiology, (Nov. 2012) vol. 78, No. 21, pp. 7572-7578 (Year: 2012).*
Lin et al., Effective inhibition of MERS-CoV infection by resveratrol. BMC infectious diseases, (Feb. 13, 2017) vol. 17, No. 1, pp. 144 ( Year: 2017).*

* cited by examiner

*Primary Examiner* — Qiuwen Mi
(74) *Attorney, Agent, or Firm* — WCF IP

(57) ABSTRACT

The present invention is from the field of disinfection and antisepsis and relates more particularly to the use of a grape extract as a virucide against viruses of the coronavirus family, adenovirus family, murine norovirus family, vaccinia virus family and poliovirus family.

3 Claims, 2 Drawing Sheets

[Fig. 1]
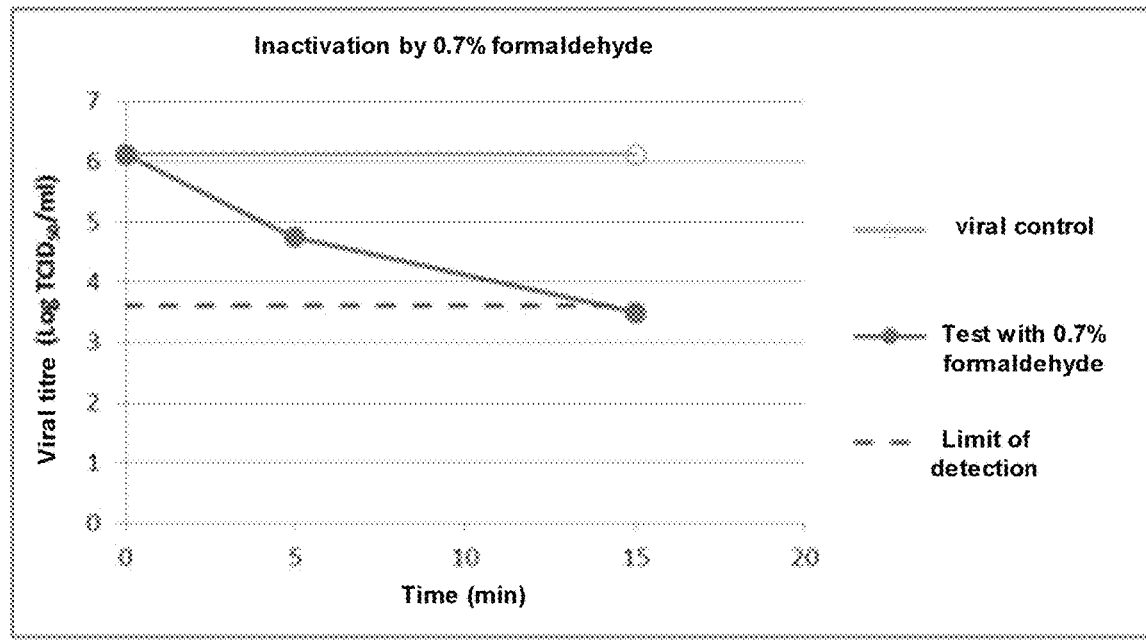
[Fig. 2]
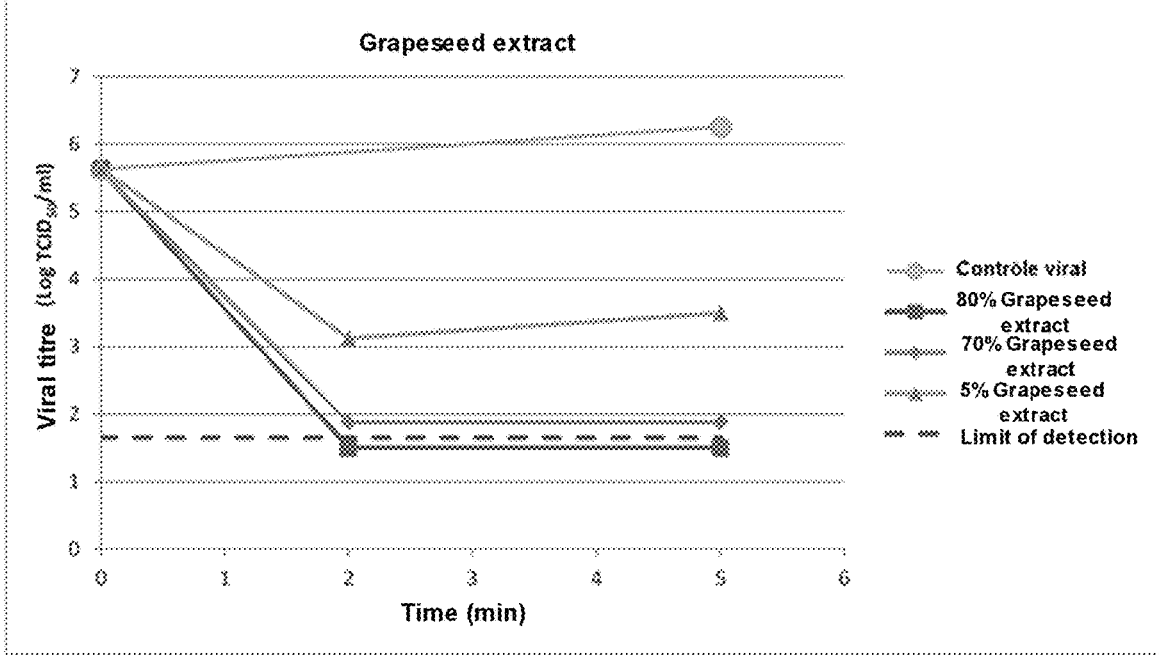

[Fig. 3]
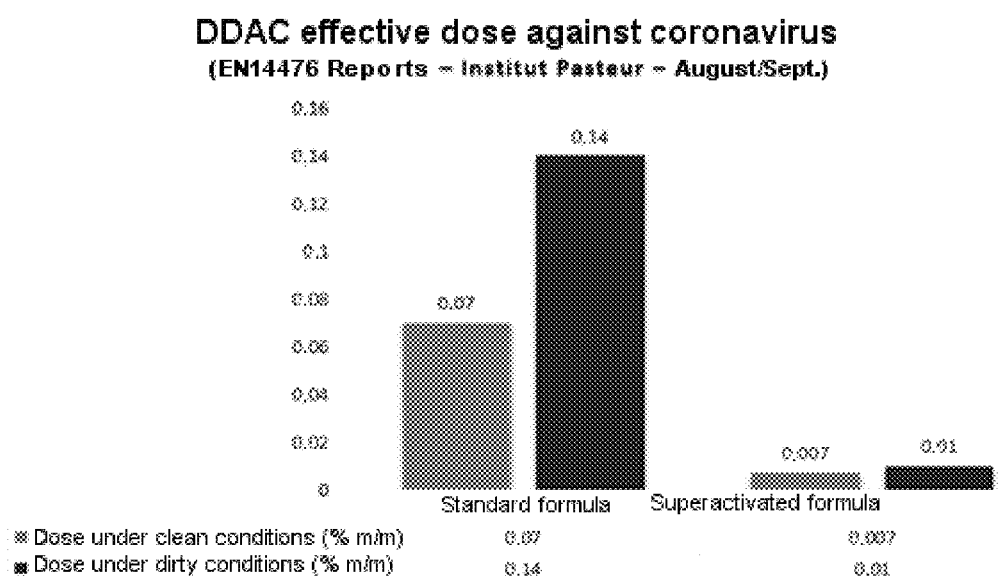

USE OF A GRAPE EXTRACT AS A VIRUCIDE AGAINST VIRUSES OF THE CORONAVIRUS FAMILY

TECHNICAL FIELD

The present invention is from the field of disinfection and antisepsis and relates more particularly to the use of a grape extract as a virucide against viruses of the coronavirus family, adenovirus family, murine norovirus family, vaccinia virus family and poliovirus family.

PRIOR ART

Disinfectant and antiseptic products are commonly used in a wide variety of products, including household and/or industrial disinfectants, but also products intended for washing keratin materials and more particularly the hands.

Disinfection is defined as a method used for inactivating the microorganisms on an inert surface (premises, object, etc.). Antisepsis is itself defined as a method used for eliminating microorganisms on living tissues such as the skin, the mucous membranes or wounds.

The study of the virucidal activity of disinfecting and antiseptic products is essential. This is because, while the bactericidal power of disinfectants and antiseptics is well studied, the virucidal activity has been studied to a much lesser degree. A disinfectant may be bactericidal without however being virucidal. In point of fact, in the context of the Covid-19 pandemic, virucidal products which have an effect on viruses of the coronavirus family are, on the one hand, necessary and, on the other hand, highly sought after.

In practice, the choice of a virucidal product must take into account various criteria of efficacy, of innocuousness (or of reduced toxicity), especially as virucidal products in the context of the pandemic are used on a very broad scale, on a very large number of users (children, adults, the elderly, etc.). The constraints are also relative to the compatibility with the materials to be treated, but also to the environmental impact. There is in fact a high demand for disinfectants and antiseptics of plant origin which thus have a low impact on health and the environment. It is also advantageous for the virucidal product to be able to have a broad spectrum and to be active against numerous enveloped and non-enveloped viruses.

The present invention relates to the use of a grape extract as an antiseptic and disinfectant, preferentially against viruses of the coronavirus family. As a plant extract, the product advantageously has a low impact on health and the environment.

In the literature, a grapeseed extract has been tested on enteric viruses (feline calicivirus, FCV-F9; murine norovirus, MNV-1, and MS2 bacteriophage) and also on the hepatitis A virus (VHA; HM175 strain).

A significant reduction in the four viruses was observed and allowed the authors to conclude that the grapeseed extract is promising for an application in the food industry as an inexpensive new natural alternative for reducing viral contamination and improving food safety.

The therapeutic activity of a grapeseed extract has also been demonstrated against the hepatitis A and C virus and respiratory syncytial virus (RSV).

However, the antiseptic and disinfectant power and more particularly the antiseptic and disinfectant power against viruses of the coronavirus family, of a grape extract, has never been demonstrated.

It has furthermore been demonstrated that the grape extract, in addition to its effect against viruses of the coronavirus family, also has an effect against viruses of the adenovirus family, murine norovirus family, vaccinia virus family and poliovirus family, thus offering a very broad spectrum.

Moreover, very specific criteria have been established for demonstrating the virucidal activity of a product. These criteria are the following:

the titre of the assay suspension is sufficient to allow a reduction of 4 log after treatment with the product;

the reduction between the logarithm of the viral control titre and that of the virus used during the reference assay for human coronavirus inactivation must be between 0.75 and 3.5 after 5 min and between 2 and 4 after 15 min (reference to the vaccinia virus, the only obligatory enveloped virus of the standard);

the cytotoxicity of the assay solution of the product affects neither cell morphology and cell growth nor sensitivity to the virus in the dilutions of the assay mixture which are required to demonstrate a reduction of 4 log in the viral titre;

during the control of the effectiveness of the stopping of the activity of the product, the difference in titre with the assay suspension must be 0.5 log;

at least one concentration per assay must show a reduction of 4 log or more and at least one concentration must show a reduction of less than 4 log.

These criteria are those of the standard EN 14476 of July 2019.

It is therefore necessary to develop a disinfectant and an antiseptic, preferentially virucidal against viruses of the coronavirus family, adenovirus family, murine norovirus family, vaccinia virus family and poliovirus family which is efficacious, and which satisfies the criteria of standard EN 14476, while at the same time having a low impact on health and the environment.

SUMMARY

It has been demonstrated by the inventors that the grape extract according to the present invention exhibits all the criteria previously mentioned, advantageously making it possible to conclude that said grape extract has virucidal activity against viruses of the coronavirus family.

The grape extract according to the present invention in fact has a virucidal activity of greater than or equal to 4.1 log against the human coronavirus strain 229E.

It has also advantageously been demonstrated that the grape extract according to the present invention also exhibits all the criteria previously mentioned, making it possible to conclude that said extract has virucidal activity against enveloped and non-enveloped viruses.

Indeed, and according to the criteria of standard EN 14476/2019, the grape extract according to the invention has virucidal activity (log R 4) against adenoviruses, murine noroviruses, vaccinia viruses and polioviruses, that is to say all enveloped and non-enveloped viruses as required in this standard.

Still advantageously, since the extract according to the invention is a plant extract, this product is efficacious while having a low impact on health and the environment.

Thus, the present invention relates to the use of a grape extract as a disinfectant against viruses of the coronavirus family.

The present invention also relates to the use of a grape extract as a disinfectant against viruses of the adenovirus family, murine norovirus family, vaccinia virus family and poliovirus family.

The present invention also relates to a method for disinfecting instruments, textiles and surfaces.

The present invention also relates to a non-therapeutic method of antisepsis comprising the application, to keratin materials, preferentially the hands, of an antiseptic composition comprising, in a physiological acceptable medium, a grape extract.

The present invention also relates to an antiseptic composition comprising, in a physiological acceptable medium, a grape extract for therapeutic use thereof as an antiseptic.

The inventors have also demonstrated that the grape extract according to the present invention has an activator effect, preferentially an activator effect on quaternary ammoniums or salts thereof. Thus, the effective dose of quaternary ammoniums or salts thereof is advantageously reduced, making it possible to provide efficacious disinfectant compositions having a lower cytotoxicity.

Thus, the present invention also relates to a disinfectant composition comprising a grape extract and a disinfectant agent chosen from a quaternary ammonium, a quaternary ammonium salt, an amine, an aldehyde, a phenol, an alcohol, peracetic acid, or mixtures thereof; said grape extract is an extract of seeds of the *Vitis vinifera* L species and is present in a content of at least 1% by weight relative to the total weight of the composition, and the disinfectant agent is present in a content of at least 1% by weight relative to the total weight of the composition.

BRIEF DESCRIPTION OF THE DRAWINGS

Other characteristics, details and advantages will emerge on reading the detailed description below, and on analysis of the appended drawings, in which:

FIG. 1 shows the viral titre (log $TCID_{50}$/ml) of a viral sample treated with 0.7% formaldehyde as a function of contact time. It is an internal control for evaluating the sensitivity of the viral sample relative to a reference product: formaldehyde.

FIG. 2 shows the viral titre (log $TCID_{50}$/ml) of a viral sample treated with a grapeseed extract according to the invention, at various concentrations (80%, 70% and 5%) as a function of contact time.

FIG. 3 shows the effective dose in terms of DDAC against coronaviruses and the activator effect of the grapeseed extract according to the invention.

DETAILED DESCRIPTION

The present invention relates to the use of a grape extract as a disinfectant against viruses of the coronavirus family.

The invention also relates to a method of disinfection against viruses of the coronavirus family.

Advantageously, the extract according to the invention has a broad virus spectrum against numerous enveloped and non-enveloped viruses. In addition to its disinfectant power against coronaviruses, it also disinfects against viruses of the adenovirus family, murine norovirus family, vaccinia virus family and poliovirus family.

Thus, the present invention also relates to the use of a grape extract as a disinfectant against viruses chosen from viruses of the coronavirus family, adenovirus family, murine norovirus family, vaccinia virus family and poliovirus family.

The invention also relates to a method of disinfection against viruses chosen from viruses of the coronavirus family, adenovirus family, murine norovirus family, vaccinia virus family and poliovirus family, comprising the application of a grape extract.

According to one embodiment, the grape extract is used as a disinfectant against viruses of the coronavirus family and, in addition, as a disinfectant against viruses of the adenovirus family, murine norovirus family, vaccinia virus family and poliovirus family.

Grape (*Vitis vinifera* L) Extract

The grape extract according to the present invention is from the *Vitis* genus and is preferentially an extract of the species *Vitis vinifera* L.

Typically, the grape extract may be obtained from the buds, flowers, fruits, leaves, grains, skin, roots, seeds.

Preferentially, the grape extract is obtained from the seeds.

Preferentially, the grape extract is obtained from the seeds of the species *Vitis vinifera* L.

The grape extract according to the present invention comprises a content of polyphenols of greater than or equal to 65%.

Typically, the polyphenols are oligomeric proanthocyanidins (OPCs). Preferentially, the content of oligomeric proanthocyanidins (OPCs) is greater than or equal to 30%.

In one embodiment, the content of oligomeric proanthocyanidins (OPCs) is greater than or equal to 90%, preferentially greater than or equal to 92%, preferentially greater than or equal to 95% and more preferably, the content of oligomeric proanthocyanidins (OPCs) is greater than or equal to 99%.

Preferentially, the content of catechin monomer is less than 5% and the content of proanthocyanidin dimers B1 is less than 8%.

According to one embodiment, the grape extract is produced from the grape seeds of the species *Vitis vinifera* L. and is obtained by a succession of extraction, purification and drying steps.

The main constituents of the grape extract according to the invention are quantified by reverse-phase high performance liquid chromatography with detection by ultraviolet absorption.

Virucidal Activity

The criteria for attesting to the virucidal activity according to standard EN 14476:2019 are the following:
- the titre of the assay suspension is sufficient to allow a reduction of 4 log after treatment with the product;
- the reduction between the logarithm of the viral control titre and that of the virus used during the reference assay for human coronavirus inactivation must be between 0.75 and 3.5 after 5 min and between 2 and 4 after 15 min (reference to the vaccinia virus, the only obligatory enveloped virus of the standard);
- the cytotoxicity of the assay solution of the product affects neither cell morphology and cell growth nor sensitivity to the virus in the dilutions of the assay mixture which are required to demonstrate a reduction of 4 log in the viral titre;
- during the control of the effectiveness of the stopping of the activity of the product, the difference in titre with the assay suspension must be 0.5 log;
- at least one concentration per assay must show a reduction of 4 log or more and at least one concentration must show a reduction of less than 4 log.

The grape extract according to the invention advantageously satisfies all these criteria, making it possible to conclude that this extract has virucidal activity against viruses of the coronavirus family, and also of the adenovirus family, murine norovirus family, vaccinia virus family and poliovirus family.

Coronavirus Family

Pathogenic human coronaviruses can be classified in the following way:
- alpha coronavirus type, which includes the 229E coronavirus (HCoV-229E) and the NL63 coronavirus (HCoV-NL63);
- beta coronavirus type: (Beta-CoV or β-CoV) divided according to the following groups: Group A comprising HCoV-0043 and HCoV-HKU1;

Group B/C comprising the highly pathogenic human coronaviruses, namely SARS-Cov-2, SARS-CoV and MERS-CoV.

The grape extract according to the present invention has a virucidal activity of greater than or equal to 4.1 log against the human strain of the 229E coronavirus.

According to one embodiment, the coronaviruses are chosen from coronaviruses of the alpha coronavirus type and coronaviruses of the beta coronavirus type.

According to one preferred embodiment, the coronaviruses are chosen from coronaviruses of the alpha coronavirus type, such as the 229E coronavirus (HCoV-229E) and the NL63 coronavirus (HCoV-NL63), coronaviruses of group A of the beta coronavirus type, such as HCoV-0043 and HCoV-HKU1, and coronaviruses of group B/C of the beta coronavirus type, such as SARS-Cov-2, SARS-CoV and MERS-CoV.

According to one preferred embodiment, the grape extract has a virucidal activity against the highly pathogenic human coronaviruses such as SARS-Cov-2, SARS-CoV and MERS-CoV, preferentially SARS-Cov-2 and MERS-CoV, and preferably SARS-Cov-2.

The human coronavirus strain 229E is an endemic strain which is known and which can be easily handled in a class II laboratory, unlike SARS-CoV-2 which is currently handled in a class III laboratory. The Haut Conseil de Santé publique [French Public Health Council] has issued various opinions and has taken into account, in order to establish its recommendations, the data described with the endemic strain of human coronavirus 229E. Typically, the survival of SARS-CoV-2 in the environment could be likened to that of other human coronaviruses such as SARS-CoV and MERS-CoV and the efficacy of the disinfection procedures on human coronaviruses such as SARS-CoV or MERS-CoV should be similar for SARS-CoV-2.

It is also recalled that most of the data have been described with the endemic strain of the human coronavirus (HCoV-229E). The data obtained on HCoV-229E could therefore be extrapolated to viruses of the coronavirus family.

Additional Microorganisms: Poliovirus, Murine Norovirus, Adenovirus and Vaccinia Virus Families Advantageously, the grape extract according to the invention has a virucidal activity against additional microorganisms such as polioviruses, murine noroviruses, adenoviruses and the vaccinia virus.

The inventors have advantageously demonstrated that the grape extract according to the invention has a virucidal activity against adenoviruses, murine noroviruses, vaccinia viruses and polioviruses.

Indeed, and according to the criteria of standard EN 14476/2019, the grape extract according to the invention has a virucidal activity (log R≥4) against adenoviruses, murine noroviruses, vaccinia viruses and polioviruses, that is to say all enveloped and non-enveloped viruses as required in this standard.

Disinfectant

The objective of a method of disinfection is to eliminate the microorganisms and/or to inactivate the virus(es) on inert surfaces such as floors, furniture, objects. This operation makes it possible to eliminate up to 99% of microorganisms.

Thus, a disinfectant is a product which makes it possible to eliminate the microorganisms and/or to inactivate the virus(es) on inert surfaces such as floors, furniture, objects, instruments.

Given its virucidal activity, the grape extract according to the invention is advantageously used as a disinfectant against viruses of the coronavirus family, but also against viruses of the adenovirus family, murine norovirus family, vaccinia virus family and poliovirus family.

Method of Disinfection

The invention also relates to a method of disinfection of a surface by means of a disinfectant composition comprising a grape extract, the method comprising the steps consisting in applying said composition to said surface.

The term "surface" is intended to mean any surface of the hospital environment, of the agri-foods industry, of shops, of restaurants, of public spaces or even surfaces in private homes. Thus, for the purposes of the present invention, the term "surface to be disinfected" is understood in the broad sense and applies to any surface that may come into contact with a patient and/or the medical staff and/or surfaces touched by different individuals, and/or food products, etc. By way of illustration of the surface, mention will be made of a floor, an instrument, an object, a piece of furniture, a material, a workbench, a piece of equipment or an element present in public transport, public furniture, a transport tool such as a container, or any other surface needing to be disinfected.

Those skilled in the art will respect the contact time required for the composition to act.

The contact time is a period of time after application that is sufficiently long to ensure destruction of the microorganisms, preferably of the viruses chosen from the coronavirus, adenovirus, murine norovirus, vaccinia virus and poliovirus families, and preferentially the viruses of the coronavirus family, which may be present on this surface. Typically, the contact time is at least thirty seconds, preferentially at least one minute, preferentially at least two minutes, preferentially at least five minutes, at ambient temperature.

Typically, the application will be carried out by airborne application or by mechanical application.

Typically, the airborne application will be carried out by an aerosol or a fumigant.

Typically, the mechanical application will be carried out by spraying, by application with wipes impregnated with the disinfectant composition, or by flooding.

According to one embodiment, the method according to the invention comprises an additional step of removing the disinfectant composition from said surface.

Typically, the removing of said composition is carried out by rinsing, for example using clear water or by dry or wet wiping.

According to one embodiment, the invention also relates to a method of disinfection of an instrument by means of a disinfectant composition comprising a grape extract, the method comprising the steps consisting in immersing the instrument to be disinfected in said disinfectant composition.

The term "instrument" is intended to mean any instrument of the hospital environment, of the agri-foods industry, of shops, of restaurants, of public spaces, or even instruments in private homes. Thus, for the purposes of the present invention, the instrument to be disinfected is understood in the broad sense and applies to any instrument that may come into contact with a patient and/or the medical staff and/or instruments touched by different individuals and/or food products, etc. By way of illustration, mention will be made of medical instruments, and transport tools such as containers.

Those skilled in the art will respect the immersion time required for the composition to act.

The immersion time is a period of time sufficiently long to ensure destruction of the microorganisms, preferably the viruses of the coronavirus family, that may be present on the instrument to be disinfected. Typically, the immersion time is at least one minute, preferentially at least two minutes, preferentially at least five minutes, preferentially at least ten minutes, preferentially at least fifteen minutes, preferentially at least twenty minutes, preferentially at least twenty-five minutes, preferentially at least thirty minutes, preferentially at least forty minutes, preferentially at least forty-five minutes, preferentially at least fifty minutes and preferably at least sixty minutes, at ambient temperature.

According to one embodiment, the method according to the invention comprises an additional step of rinsing, for example with clear water.

The invention also relates to a method of disinfection of a textile by means of a disinfectant composition comprising a grape extract, the method comprising the steps consisting in applying said composition to said textile or immersing said textile in said disinfectant composition.

The term "textile" is intended to mean any textile of the hospital environment, of the agri-foods industry, of shops, of restaurants, of public spaces, such as the textiles present on public transport, or even textiles in private homes. Thus, for the purposes of the present invention, the textile to be disinfected is understood in the broad sense and applies to any textile that may come into contact with a patient and/or the medical staff and/or food products and/or textiles touched by different individuals and/or textiles in daily life.

Those skilled in the art will respect the contact time or the immersion time required for the composition to act.

The contact time is a period of time after application that is sufficiently long to ensure destruction of the microorganisms, preferentially of the viruses chosen from the coronavirus, adenovirus, murine norovirus, vaccinia virus and poliovirus families, and preferentially the viruses of the coronavirus family, that may be present on the textile to be disinfected. Typically, the contact time is at least one minute, preferentially at least two minutes, preferentially at least five minutes, preferentially at least ten minutes, preferentially at least fifteen minutes, and preferentially at least twenty minutes, at ambient temperature.

Typically, the immersion time is at least one minute, preferentially at least two minutes, preferentially at least five minutes, preferentially at least ten minutes, preferentially at least fifteen minutes, preferentially at least twenty minutes, preferentially at least twenty-five minutes, preferentially at least thirty minutes, preferentially at least forty minutes, preferentially at least forty-five minutes, preferentially at least fifty minutes and preferably at least sixty minutes, at ambient temperature.

According to one embodiment, the method according to the invention comprises an additional step of rinsing, for example with clear water.

Disinfectant Composition

The disinfectant composition comprises, in an aqueous or aqueous-alcoholic medium, a grapeseed extract according to the invention.

According to one embodiment, the content of grape extract is at least 0.2% by weight relative to the total weight of the composition, preferentially at least 0.5% by weight relative to the total weight of the composition, preferentially at least 1% by weight relative to the total weight of the composition, preferentially at least 2% by weight relative to the total weight of the composition, preferentially at least 3% by weight relative to the total weight of the composition, preferentially at least 4% by weight relative to the total weight of the composition, preferentially at least 5% by weight relative to the total weight of the composition.

According to one embodiment, the disinfectant composition will also comprise at least one agent chosen from non-ionic surfactants, antifoams, anionic surfactants, water-soluble polymers, chelating agents, agents for treating a metal surface, acids, preserving agents, stabilizers, optical-effect products, enzymes, waxes, waxy emulsions, descaling agents, cationic surfactants, disinfectants.

Among the non-ionic surfactants, mention will be made of ethoxylated alcohols, alkylpolyglucosides, ethoxylated ammoniums, low-foaming non-ionic surfactants, polyalkylene glycols.

Among the anionic surfactants, mention will be made of fatty alcohol ether sulfates, fatty alcohol sulfates, linear alkyl benzene sulfonates.

Among the water-soluble polymers, mention will be made of dispersants, thickeners.

Among the agents for treating a metal surface, mention will be made of corrosion inhibitors.

Among the preserving agents, mention will be made of bronopol, formic acid, glutaraldehyde, glyoxal, n-propanol, phenoxyethanol, dichlorohydroxydiphenyl ether (DCPP).

Among the optical-effect products and the stabilizers, mention will be made of antioxidants, excited blocking agents (ESQ™) (UV stabilizers), optical brighteners, UV stabilizers.

Among the enzymes, mention will be made of cellulases, proteases.

Among the descaling agents, mention will be made of phosphonates or polyphosphonates.

Among the disinfectants, mention will be made of quaternary ammoniums, quaternary ammonium salts, amines, aldehydes, phenols such as ortho-phenylphenol, alcohols, peracetic acid, or mixtures thereof.

Activating Effect of the Grape Extract

According to one embodiment, the grape extract according to the invention is combined with a disinfectant agent chosen from a quaternary ammonium, a quaternary ammonium salt, an amine, an aldehyde, a phenol such as ortho-phenylphenol, an alcohol, peracetic acid, or mixtures thereof.

Among the quaternary ammoniums and quaternary ammonium salts, mention may be made of alkyldimethylbenzylammonium chloride (ADBAC, BKC), the tetramethylammonium cation (TMAC), N-(3-aminopropyl)-N-dodecylpropane-1,3-diamine (diamine), N,N-didecyl-N-methylpoly(oxyethyl)ammonium propionate (Bardap26), didecyldimethylammonium chloride (DDAC).

It has in fact been demonstrated that the grape extract according to the invention has an activating effect on quaternary ammoniums and/or quaternary ammonium salts and thus makes it possible to reduce the dose of quaternary ammoniums and/or of quaternary ammonium salts in the disinfectant composition.

Advantageously, the decrease in the amount of quaternary ammoniums and/or of quaternary ammonium salts makes it possible to obtain an efficacious disinfectant composition having reduced cytotoxicity.

Preferentially, the grape extract is combined with didecyldimethylammonium chloride (DDAC).

Thus, the present invention also relates to a disinfectant composition comprising a grape extract, a quaternary ammonium and/or a quaternary ammonium salt, said grape extract being present in a content of at least 1% by weight relative to the total weight of the composition and the quaternary ammonium and/or the quaternary ammonium salt is chosen from alkyldimethylbenzylammonium chloride (ADBAC, BKC), the tetramethylammonium cation (TMAC), N-(3-aminopropyl)-N-dodecylpropane-1,3-diamine (diamine), N,N-didecyl-N-methylpoly(oxyethyl)ammonium propionate (Bardap26), and didecyldimethylammonium chloride (DDAC) and is present in a content of at least 1% by weight relative to the total weight of the composition.

The present invention also relates to a disinfectant composition comprising a grape extract and a quaternary ammonium salt; said grape extract is an extract of seeds of the species *Vitis vinifera* L and is present in a content of at least 1% by weight relative to the total weight of the composition and the quaternary ammonium salt is didecyldimethylammonium chloride and is present in a content of at least 1% by weight relative to the total weight of the composition.

Antiseptic

An antisepsis method applies to the disinfection of living tissues: skin, scalp, skin appendages, mucous membranes and wounds. The products concerned are for preventive or curative external use. Thus, an antiseptic is a product which makes it possible to disinfect living tissues.

Antisepsis Method: Non-Therapeutic

Thus, the present invention relates to a non-therapeutic antisepsis method, characterized in that it comprises the application to the keratin materials of an antiseptic composition comprising, in a physiologically acceptable medium, a grape extract.

Typically, the keratin materials will be the skin, the scalp, the skin appendages and the mucous membranes, preferentially the skin and most preferentially the skin of the hands.

Typically, the application of the antiseptic composition during the antisepsis method can be carried out for hygienic treatment of the hands by friction or hygienic washing of the hands.

Antiseptic Composition: Therapeutic

According to one embodiment, the present invention relates to a therapeutic method for wound antisepsis.

Thus, the present invention relates to a grape extract for use thereof in a therapeutic method for disinfection of keratin materials.

The present invention also relates to a therapeutic method for disinfection of keratin materials comprising the application of a grape extract.

Typically, the therapeutic method for disinfection applies to wounds of the keratin materials, preferentially the skin and the mucous membranes.

The present invention also relates to an antiseptic composition comprising, in a physiologically acceptable medium, a grape extract for use thereof in a therapeutic method for disinfection of keratin materials.

The present invention also relates to the use of an antiseptic composition comprising, in a physiologically acceptable medium, a grape extract for the production of a medicament intended for the disinfection of keratin materials.

The present invention also relates to the use of an antiseptic composition comprising, in a physiologically acceptable medium, a grape extract for disinfection of keratin materials.

The present invention also relates to an antisepsis method comprising the application to the keratin materials of a patient, of an antiseptic composition comprising, in a physiologically acceptable medium, a grape extract.

The term "physiologically acceptable" denotes a medium which does not exhibit any harmful side effects and in particular which does not produce redness, inflammation, heating, tautness or tingling that are unacceptable for the user of the product. The medium is thus compatible with the keratin materials of human beings.

The antiseptic composition may be in any of the galenical forms used in this field and normally used for antiseptic topical application, such as aqueous, aqueous-alcoholic or oily solutions, solutions or dispersions of the lotion or serum type, emulsions of liquid or semi-liquid consistency of the milk type, which are obtained by dispersion of a fatty phase in an aqueous phase (O/W) or vice versa (W/O), suspensions or emulsions which have a soft, semi-solid or solid consistency, of the cream or aqueous or anhydrous gel type, anhydrous compositions, microparticles or vesicular dispersions of ionic and/or non-ionic type. These compositions are prepared by the usual methods known to those skilled in the art.

According to one embodiment, the compositions according to the invention are in the form of an aqueous single-phase solution, in the form of an aqueous-alcohol single-phase solution, in the form of an aqueous-alcoholic or aqueous gel, or in the form of an oil-in-water or water-in-oil, preferentially oil-in-water, emulsion. The term "aqueous single-phase solution" is intended to mean a composition comprising an aqueous continuous phase comprising water and, optionally, one or more water-miscible organic solvents.

The term "aqueous-alcoholic single-phase solution" is intended to mean a composition comprising a continuous aqueous-alcoholic phase comprising at least one alcohol, and according to one aspect, several alcohols miscible with one another.

Among the galenical forms, in the form of aqueous or aqueous-alcoholic single-phase compositions suitable for an antiseptic topical application to keratin materials, preferentially the skin, mention will be made of shower gels, liquid cleansers, lotions, and gels.

Typically, these galenical forms may be used for hygienic treatment of the hands by friction or hygienic washing of the hands.

The term "emulsion" is intended to mean compositions comprising an aqueous phase and an oily phase dispersed in one another, for example water-in-oil (W/O) or oil-in-water (O/W) or multiple (W/O/W or O/W/O) emulsions.

According to one embodiment, the composition is in the form of a water-in-oil emulsion.

The water-in-oil (W/O) emulsions comprise an aqueous phase dispersed in an oily phase. These emulsions comprise an oily continuous phase.

According to one embodiment, the composition is in the form of an oil-in-water emulsion. These emulsions comprise an oily phase dispersed in an aqueous phase. These emulsions comprise an aqueous continuous phase.

Among the galenical forms in the form of oil-in-water or water-in-oil emulsions, mention will be made of creams, washing creams, foams and milks.

Typically, these galenical forms may be used for hygienic treatment of the hands by friction or hygienic washing of the hands, but also, when present in the form of a cream, for the care of hands damaged for example by frequent washing. The antiseptic cream will have an antiseptic power and advantageously a restorative power through the presence of moisturizing compounds.

According to one embodiment, the compositions according to the invention are in the form of a gel, in order, for example, to enable their distribution either by pouring from a bottle, or by pressure on a flexible tube, or by pressure exerted on the pump of a pump dispenser bottle.

The disinfectant composition according to the invention also comprises any pharmaceutically acceptable additive.

The term "pharmaceutically acceptable" is intended to mean a substance which is not biologically undesirable or undesirable in another way, that is to say which can be incorporated into a pharmaceutical composition administered to a patient without causing undesirable biological effects or without interacting in a harmful way with one of the other components of the composition which contains it, for example by inhibiting or reducing the antiviral properties of the grape extract according to the invention. When the term "pharmaceutically acceptable" is used to denote a carrier or a pharmaceutical excipient, it is implied that the carrier or the excipient meets the required standards in terms of toxicological and manufacturing tests.

Typically, the pharmaceutically acceptable excipient may be chosen from a humectant, a diluent, a disintegrating agent, a binder, a slip agent, a lubricating agent, a wetting agent, a buffering agent, a suspending agent, an adjuvant, an emulsifier, an absorbent, a preserving agent, a surface agent, an antioxidant, an oil, a wax, a gelling agent, an emulsifying agent, a surfactant or a mixture thereof.

Humectant

The composition according to the invention may comprise at least one humectant.

The humectant may be chosen from polyols and/or esters of fatty acids and of polyethylene glycol.

The term "polyols" is intended to mean any molecule having in its structure at least two free hydroxyl groups (—OH). These polyols are preferably liquid at ambient temperature (25° C.).

Typically, the polyol will be chosen from maltitol, mannitol, xylitol, erythritol, sorbitol, isosorbide, glycerol or glycerin, glucose, sucrose, polydextrose, hydrogenated glucose syrups, dextrins, maltodextrins, glucose syrups, and mixtures thereof.

According to one embodiment, the polyol is glycerin.

Oil

The composition according to the invention comprises at least one oil.

For the purposes of the present invention, the term "oil" is intended to mean a compound which is liquid at ambient temperature (25° C.), and which, when it is introduced in a proportion of at least 1% by weight in water at 25° C., is not at all soluble in water, or is soluble in an amount of less than 10% by weight, relative to the weight of oil introduced into the water.

According to one embodiment, the oil will be chosen from volatile oils, non-volatile oils, and mixtures thereof.

The liquid fatty phase advantageously comprises one or more non-volatile oils which provide an emollient effect on the skin.

Among the non-volatile oils, mention may be made of fatty esters, $C_{12}$ to $C_{15}$ alkyl benzoates, glycol esters, higher fatty acids such as myristic acid, palmitic acid, stearic acid, behenic acid, oleic acid, linoleic acid, linolenic acid or isostearic acid, plant oils such as avocado oil, camelia oil, hazelnut oil, Tsubaki oil, cashew nut oil, argan oil, soybean oil, grapeseed oil, sesame oil, corn oil, wheatgerm oil, rapeseed oil, sunflower oil, cotton seed oil, jojoba oil, peanut oil, macadamia oil, sweet almond oil, olive oil, and mixtures thereof, plant butters such as shea butter, camelia butter, and mineral oils.

These non-volatile oils may also be oils of hydrocarbon or silicone type, such as liquid paraffin, squalene oil, liquid petroleum jelly, dimethylsiloxanes, and mixtures thereof.

Typically, the oil may be a mineral oil.

Wax

The term "wax" is intended to mean a fatty substance with a reversible liquid/solid change of state, having a melting point of greater than 30° C. and generally less than 90° C., which is liquid under the conditions for preparing the composition and which, in the solid state, has an anisotropic crystalline organization.

The waxes may in particular be chosen from animal waxes, plant waxes and synthetic or silicone waxes containing polar groups, such as esters.

Gelling Agent

The term "gelling agent" is intended to mean a compound which, in the presence of a solvent, creates intermacromolecular bonds which are more or less strong, thus inducing a three-dimensional network which sets said solvent.

The gelling agent is chosen from hydrophilic organic gelling agents, and/or lipophilic organic gelling agents, and/or amphiphilic organic gelling agents, and/or mineral gelling agents.

Binder

The term "binder" is intended to mean compounds which confer increased cohesion on the cosmetic composition. This cohesion can be adjusted according to the amount and chemical affinity of the binding agent relative to the ingredients of the cosmetic composition.

Emulsifying Agent

The composition may comprise one or more oil-in-water (O/W) or water-in-oil (W/O) emulsifiers.

The oil-in-water (O/W) emulsifier is an emulsifying agent with an HLB of greater than or equal to 8 and chosen from optionally polyethoxylated sorbitan esters, fatty acid esters of glycerol, fatty acid esters or polyesters of sucrose, fatty acid esters of polyethylene glycol, polyether-modified polysiloxanes, fatty alcohol ethers of polyethylene glycol, alkylpolyglycosides and hydrogenated lecithin, fatty alcohols, sorbitan esters, mixtures of fatty alcohol and of phosphate esters, without this list being limiting, and mixtures thereof.

The water-in-oil (W/O) emulsifier is an emulsifying agent with an HLB of less than 8 and chosen from non-ethoxylated fatty esters of polyols and in particular from non-ethoxylated fatty esters of glycerol, of polyglycerols, of sorbitol, of sorbitan, of anydrodrohexitols such as in particular isosorbide, of mannitol, of xylitol, of erythritol, of maltitol, of sucrose, of glucose, of polydextrose, of hydrogenated glucose syrups, of dextrins and of hydrolysed starches.

Surfactant

The composition may comprise a surfactant chosen from ionic, non-ionic, anionic or amphoteric or zwitterionic surfactants. These surfactants are chosen for their detergent and foaming function.

Active Ingredients

The composition according to the invention may comprise at least one other active ingredient. By way of illustration, mention will be made of an antibacterial agent, an antifungal agent, an anti-irritant, an antioxidant, a free-radical scavenger, a healing agent, a moisturizing agent, an emollient, vitamins, minerals.

Preferentially, the composition will comprise a moisturizing agent.

EXAMPLES

Example 1: Demonstration of the Virucidal Activity of a Grapeseed Extract According to the Invention Against Coronavirus Experimental Conditions
Duration of the test: from 06/08/2020 to 18/08/2020
Dilution product: hard water
Concentrations tested: 5% (i.e. 0.2% of extract), 70% (i.e. 2.8% of extract) and 80% (i.e. 3.2% of extract). These doses are obtained after dilution of a solution of grape extract at 4% in water.
Appearance of the diluted product: brown
Contact time: 2 and 5 minutes
Temperature of the test: 20° C.
Interfering substance: solution of bovine albumin (BSA) at 0.3 g/l
Strain: strain of human coronavirus 229E (HCoV-229E)
Cell line: Huh-7 cells, DMEM+Glutamax™ supplemented with 10% of foetal calf serum (FCS) and 1% of antibiotics
Incubation: 6 days at 33° C. with 5% $CO_2$
Quantification method: microtitration plates ($TCID_{50}$/ml with the Spearman-Karber calculation method)
Principle of the Test A sample of the product diluted in hard water is added to a virus assay suspension, in a solution of an interfering substance. The mixture is maintained at 20° C. for 2 and 5 minutes. An aliquot portion is removed at the end of these contact times. The virucidal activity is immediately eliminated according to a validated method (filtration on an S400 HR MicroSpin™ column and dilution in an ice-cold medium). The dilutions are transferred into the cell culture units. After incubation, the infectious titre is calculated according to the Spearman-Karber calculation method. The reduction in infectivity of the virus is calculated and corresponds to the difference between the titres of the virus (viral control), expressed in log, before and after the treatment with the product. The test was carried out on strains of the human coronavirus 229E (HCoV-229E).

Results

1. Controls i) Determination of the Cytotoxicity of the Product

The cytotoxicity corresponds to the morphological modification of the cells preventing visualization of the cytopathogenic effect. After neutralization, successive dilutions of the product subjected to the assay are brought into contact with the cells in order to evaluate their cytotoxicity.

TABLE 1

| Test concentration (%) | Tested filtrate dilutions | | | |
|---|---|---|---|---|
| 80 | $10^{-1}$ | $10^{-2}$ | $10^{-3}$ | $10^{-4}$ |
| 70 | — | — | — | — |
| 5 | — | — | — | — |

—: absence of cytotoxicity (cell carpet intact); C: presence of a cytotoxic effect.

Conclusion

After filtration on a MicroSpin™ S400 HR column, the $10^{-1}$ dilution no longer exhibits any cytotoxic activity for the Huh-7 cells for the product at 80%, at 70% and at 5%.

The grape extract according to the invention does not show any cytotoxic effect.

ii) Determination of the Sensitivity of the Cells to the Virus

The purpose of the interference control is to verify that the sensitivity of the cells to the viral infection is not negatively influenced by the treatment with the product assay solution. The sensitivity of the cells to the virus is assessed by comparison of two titrations of the stock suspension of the virus: one obtained on cells treated for 1 h with the lowest apparently non-cytotoxic dilution of the product, the other on non-treated cells.

TABLE 2

| | | Viral titre (log $TCID_{50}$/ml) | | |
|---|---|---|---|---|
| Concentrations tested (%) | Subcytotoxic concentration (dilution of the filtrate) | Viral suspension cultured on cells treated at the subcytotoxic concentration | Viral suspension cultured on non-treated cells | Difference of viral titre |
| 80 | $10^{-1}$ | 6.6 | 6.8 | 0.1 |
| 70 | $10^{-1}$ | 6.4 | | 0.4 |
| 5 | $10^{-1}$ | 6.4 | | 0.4 |

The difference between these two titres must be less than or equal to 1 log in order for the assay for sensitivity of the cells to the virus to be validated.

Conclusion

The products at 80%, 70% and 5% allow a correct titration of the human coronavirus 229E.

iii) Control of the Efficacy of the Virucidal Activity Suppression

This control makes it possible to verify that the filtration on a MicroSpin™ S400 HR column is capable of stopping the virucidal activity of the product.

TABLE 3

| | Viral titre (log TCID$_{50}$/ml) | | |
|---|---|---|---|
| Concentrations tested (%) | Filtration on MicroSpin ™ S400 HR column then contacting with the viral suspension (dilution and pause for 30 min on ice before titration) | Control viral suspension | Difference in viral titre |
| 80 | 6.6 | 6.8 | 0.1 |
| 70 | 6.5 | | 0.3 |
| 5 | 6.6 | | 0.1 |

The difference in titre with the suspension test must be 0.5 log.

Conclusion

The MicroSpin™ S400 HR column filtration technique clearly makes it possible to stop the virucidal activity of the product.

iv) Reference Viral Inactivation Test

This internal control for the assay makes it possible to evaluate the sensitivity of the virus batch compared to a reference product: 1.4% (m/V) formaldehyde.

TABLE 4

| | Viral titre (log TCID$_{50}$/ml) | Reduction in viral titre |
|---|---|---|
| Control viral suspension | 6.1 | — |
| Assay for inactivation after 5 minutes of contact | 4.8 | 1.4 |
| Assay for inactivation after 15 minutes of contact | ≤3.5 | ≥2.6 |

The reduction between the logarithm of the titre of the viral control and that of the virus used during the reference assay for the inactivation of enveloped viruses must be between 0.75 and 3.5 log after 5 min and between 2 and 4 log after 15 min.

The results are presented in FIG. 1.

Conclusion

The sensitivity of the viral suspension used for the test is in accordance with the recommendations of the standard.

2. Evaluation of the Virucidal Activity

Principle

The grape extract (at a given concentration) is brought into contact with the viral suspension and the interfering substance. The reaction is stopped by filtration on a MicroSpin™ S400 HR column after the required contact time and then dilution under cold conditions. The titre of each assay is determined, expressed in logarithm of cytotoxic infectious dose capable of infecting 50% of the cells (Log DICT$_{50}$), and calculated according to the Spearman and Kärber method, described in annex C of the standard EN 14476 of July 2019. The limit of detection of the titration technique corresponds to the theoretical minimum titre resulting from the detection of a viral particle in the first dilution tested. The limit of detection depends on the proportion and the volume tested of this dilution.

Results i. Viral Titre

TABLE 5

| | Viral titre in log TCID$_{50}$/ml (confidence interval at 95%) |
|---|---|
| Before filtration on MicroSpin ™ S400 HR column | 6.8 (±0.3) |
| After filtration on MicroSpin ™ S400 HR column | 6.6 (±0.3) |

The MicroSpin™ S400 HR column does not reduce the infectivity of the virus (overlapping confidence intervals).

TABLE 6

| | Viral titre in log TCID$_{50}$/ml in the solution tested after . . . minutes | | |
|---|---|---|---|
| | 0 | 2 | 5 |
| Virus assay suspension | 5.6 (±0.3) | 5.5 (±0) | 5.5 (±0) |

Given the level of cytotoxicity of the product, and the dilution for stopping the reaction, the limit of detection is 1.5 log DICT$_{50}$/ml for all the concentrations. With an initial titre at 5.6 log DICT$_{50}$/ml, the maximum virucidal activity that can be quantified in this assay is 4.1 log.

TABLE 7

| Product | Concentration in the assay (%) | Log TCID$_{50}$/ml in the assay solution after . . . minutes | |
|---|---|---|---|
| | | 2 | 5 |
| Grapeseed extract according to the invention | 80 | ≤1.5 (±0) | ≤1.5 (±0) |
| | 70 | 1.9 (±0.4) | 1.9 (±0.4) |
| | 5 | 3.1 (±0.4) | 3.5 (±0) |
| Assay viral control | n.a. | 5.6 (±0.3) | 5.6 (±0.3) |

These results are represented in FIG. 2.

ii. Reduction

TABLE 8

| Product | Concentrations in the assay (%) | Reduction (log TCID$_{50}$/ml) in the assay after . . . minutes | |
| --- | --- | --- | --- |
| | | 2 | 5 |
| Grapeseed extract according to the invention | 80 | ≥4.1 (±0.3) | ≥4.1 (±0.3) |
| | 70 | 3.8 (±0.5) | 3.8 (±0.4) |
| | 5 | 2.5 (±0.4) | 2.1 (±0.3) |

Conclusion

The grapeseed extract according to the present invention has a virucidal activity of greater than or equal to 4.1 log against the human strain of the coronavirus 229E at the concentrations tested for a contact time of 2 or 5 minutes, under clean conditions.

3) Verification of the Methodology

A test is considered to be valid when the following criteria are met:
- The titre of the assay suspension is sufficient to allow a reduction of 4 log after treatment with the product;
- The reduction between the logarithm of the titre of the viral control and that of the virus used during the reference assay for inactivation of the human coronavirus must be between 0.75 and 3.5 after 5 min and between 2 and 4 after 15 min (reference to the vaccinia virus, the only obligatory enveloped virus of the standard);
- The cytotoxicity of the assay solution of the product affects neither cell morphology and cell growth nor sensitivity to the virus in the dilutions of the assay mixture which are required to demonstrate a reduction of 4 log in the viral titre;
- During the control of the efficacy of the stopping of the activity of the product, the difference in titre with the assay suspension must be 0.5 log;
- At least one concentration per assay must show a reduction of 4 log or more and at least one concentration must show a reduction of less than 4 log.

In the context of this assay, all of the criteria are met.

Conclusion

The grapeseed extract according to the present invention advantageously has a virucidal activity against the viruses of the coronavirus family. The grapeseed extract according to the invention is advantageously efficacious against viruses of the coronavirus family and is non-cytotoxic. The grapeseed extract according to the present invention thus makes it possible to provide disinfectants and antiseptics of plant origin which have a low impact on health and the environment.

Example 2: Activating Effect of the Grape Extract According to the Invention

Two aqueous-phase formulas were tested for their efficacy against the beta coronavirus:
- an aqueous solution comprising 7% of DDAC,
- an "activated" aqueous solution comprising 1% of DDAC and 1% of a grape extract.

The results obtained according to the methodology, presented above, of the standard EN14476, are presented in the table below in order to detect the DDAC effective dose having a virucidal activity on the beta coronavirus.

TABLE 9

| Conditions | Standard formula | | Superactivated formula | |
| --- | --- | --- | --- | --- |
| Temperature = 20° C. Contact times = 5 min clean conditions | DDAC effective dose | 0.07% (dilution formula in 1% water) | DDAC effective dose | 0.007% (dilution formula in 0.7% water) |
| | DDAC cytotoxic dose | 0.14% (dilution formula in 2% water) | DDAC cytotoxic dose | 0.035% (dilution formula in 3.5% water) |
| Temperature = 20° C. Contact times = 5 min dirty conditions | DDAC effective dose | 0.07% (dilution formula in 1% water) | DDAC effective dose | 0.01% (dilution formula in 1% water) |
| | DDAC cytotoxic dose | 0.14% (dilution formula in 2% water) | DDAC cytotoxic dose | 0.035% (dilution formula in 3.5% water) |

Advantageously, the grape extract according to the invention is an activator of DDAC and makes it possible to reduce the effective and useful dose of DDAC by a factor of 10, this being as represented in FIG. 3.

Example 3: Disinfectant Composition

In this example, a disinfectant composition is reproduced in table 10 below.

TABLE 10

| Ingredients | Amount (in percentage %) |
| --- | --- |
| Biobased solvent derived from glycerol | 20 |
| DDAC | 1 |
| Grape extract | 1 |
| Biobased ethoxylated alcohol | 2.7 |
| Biobased surfactant such as polysorbate | 1.8 |
| Water | qs |

The composition may be applied on a surface or a textile or may be used to immerse an instrument or a textile in a method of disinfection.

Example 4: Antiseptic Composition in the Form of a Gel

In this example, an antiseptic composition in the form of an aqueous-alcoholic gel is reproduced in table 11 below.

TABLE 11

| Ingredients | Amount (in percentage %) |
| --- | --- |
| Water | qs |
| Alcohol | 10 |
| Glycerin | 1.5 |
| Neutralized acrylates/C10-30 alkyl acrylate crosspolymer | 0.5 |
| Grape extract | 3 |

Typically, the antiseptic composition may be used for hygienic treatment of the hands by friction or hygienic washing of the hands.

Example 5: Antiseptic Composition in the Form of a Cream

In this example, an antiseptic composition in the form of a cream is reproduced in table 12 below.

TABLE 12

| Ingredients | Amount (in percentage %) |
| --- | --- |
| Water | qs |
| Emulsifier | 3.5 |
| Wax | 3.0 |
| Thickener | 1.0 |
| Isostearyl isostearate | 4.0 |
| Mineral oil | 3.0 |
| Glycerin | 4.0 |
| Grape extract | 3 |

Typically, the cream may be used for the care of hands damaged for example by frequent washing. The antiseptic cream in fact has an antiseptic power and advantageously a restorative powder through the presence of these moisturizing agents.

Example 6: Demonstration of the Virucidal Activity of a Grapeseed Extract According to the Invention Against Viruses of the Adenovirus Family, Murine Norovirus Family, Vaccinia Virus Family and Poliovirus Family The virucidal activity of the grapeseed extract according to the invention was evaluated according to the criteria of the standard EN14476:2019 as described above.

Products Tested:

| Dilution | Preparation |
| --- | --- |
| 97% | product as such |
| 80% | product as such |
| 5% | 6.25% (v/v) solution in distilled water |

Conditions of the Test

| Strains tested (standard) | Cell lines for propagation of the tested strains |
| --- | --- |
| Adenovirus type 5, strain Adenoid, 75 ATCC VR-5 | HeLa, ATCC CCL.2 |
| Murine norovirus MNV, strain 599 Berlin Friedrich Loeffler Institute RVB-0651 | Raw 264.7 ATCC TIB-71 |
| Poliovirus type 1 LSc-2ab, Eurovir Hygiene Institute | LLC-MK2 ATCC CCL-7.1 |
| Vaccinia virus, strain Ankara, ATCC-VR-1508 | BHK-21-cl 13, IZS-Brescia |
| Contact time | 5 min ± 10 seconds |
| Test temperature | 20° C. ± 1° C. |
| Interfering substance | Bovine albumin 0.3 g/l (clean conditions) |
| Incubation conditions | 37° C. ± 1° C., 5% $CO_2$ |

Materials and Reagents:

Growth medium: MEM 10% FCS

Growth medium: MEM 2% FCS

According to the criteria of the standard EN 14476/2019, the grape extract according to the invention has a virucidal activity (log R 4) when it is used at 97% and at 80% against adenoviruses, murine noroviruses, the vaccinia virus and polioviruses. According to this same standard, a virucidal activity can therefore be claimed.

Example 6: Demonstration of the Antiseptic Effect of a Composition According to the Invention The antiseptic power of a cream comprising an extract according to the invention was evaluated and compared to the same cream not comprising the extract according to the invention. The compositions of the creams are described below:

| Ingredient | Cream comprising the extract according to the invention | Control |
| --- | --- | --- |
| Grapeseed extract | 4% | 0% |
| Caprylic/capric triglyceride (emollient) | 10% | 10% |
| Cetaryl alcohol (and) dicetyl phosphate (and) ceteth-10 phosphate (O/W emulsifier) | 5% | 5% |
| Glycerin (moisturizing agent) | 5.5% | 5.5% |

-continued

| Ingredient | Cream comprising the extract according to the invention | Control |
| --- | --- | --- |
| Xanthan gum (thickener) | 0.5% | 0.5% |
| NaOH for adjusting the pH to 5 | 0.3% | 0.3% |
| Water | Qs 100% | Qs 100% |

The protocol is the following:

A sample of 1 gram of each product (cream with extract and cream without extract) is, beforehand, removed from its container and placed in sterile jars, under aseptic conditions; three repetitions are carried out per product.

Each product is artificially contaminated with the same stock suspension of virus by depositing 100 µl as micro droplets with a virus concentration of $1\times10^7$ $DICT_{50}$/ml.

At the end of the contact time of 2 minutes or 30 minutes, each product is mixed with a universal neutralizer in order to stop the action of the active ingredient. The entire mixture is stirred with glass beads for 1 min using a vortex, and then incubated for 30 minutes at ambient temperature in order to give the neutralizer time to act. At the end of the 30 minutes of neutralization, each mixture is placed in a Stomacher® homogenization bag with sterile side filter for recovering the solution of virus to be analysed, freed of the product debris, and centrifuged for 10 minutes in order to remove the remaining debris.

After centrifugation, the supernatant is recovered and then filtered through a filter with a porosity of 0.20 µm. After filtration, the solution containing the viruses is passed over a Microspin™ column in order to remove the cytotoxicity induced by the cream. After having been passed over a Miccrospin™ column, the solution is concentrated on an Amicon® column. The viruses are then quantified on permissive cells.

The efficacy criteria are the same as those of EN14476.

Advantageously, the cream comprising the extract according to the invention allows the virucidal activity to be decreased, compared to the control cream, making it possible to conclude that the extract and the cream comprising the extract according to the invention have antiseptic power.

Subject of the Invention

1. Use of a grape extract as a disinfectant against viruses chosen from the viruses of the coronavirus family, adenovirus family, murine norovirus family, vaccinia virus family and poliovirus family.

2. Use according to claim 1, characterized in that the disinfectant is disinfectant against viruses of the coronavirus family.

3. Use according to claim 2, characterized in that the extract is also disinfectant against viruses of the adenovirus family, murine norovirus family, vaccinia virus family and poliovirus family.

4. Use according to any one of claims 1 to 3, characterized in that the grape extract is an extract of seeds of the species Vitis vinifera L.

4. Method of disinfection of a surface, of an instrument or of a textile by means of a disinfectant composition comprising a grape extract, the method comprising the steps consisting in applying said composition to said surface or said textile or in immersing said instrument or said textile in said composition.

6. Method of disinfection, characterized in that the disinfectant composition comprises at least 0.2% by weight relative to the total weight of the composition of a grapeseed extract.

7. Method of disinfection, characterized in that the disinfectant composition also comprises at least one quaternary ammonium or one quaternary ammonium salt chosen from alkyldimethylbenzylammonium chloride (ADBAC, BKC), the tetramethylammonium cation (TMAC), N-(3-aminopropyl)-N-dodecylpropane-1,3-diamine (diamine), N,N-didecyl-N-methylpoly(oxyethyl)ammonium propionate (Bardap26) and didecyldimethylammonium chloride (DDAC).

8. Non-therapeutic antisepsis method, characterized in that it comprises the application to keratin materials of an antiseptic composition comprising, in a physiologically acceptable medium, a grape extract.

9. Antiseptic composition comprising, in a physiologically acceptable medium, a grape extract for therapeutic use thereof as an antiseptic.

10. Antiseptic composition, characterized in that said composition is in the form of an aqueous single-phase solution, in the form of an aqueous-alcoholic single-phase solution, in the form of an aqueous-alcoholic or aqueous gel, or in the form of an emulsion.

11. Disinfectant composition comprising a grape extract and a disinfectant agent chosen from a quaternary ammonium, a quaternary ammonium salt, an amine, an aldehyde, a phenol, an alcohol, peracetic acid, or mixtures thereof, said grape extract being present in a content of at least 1% by weight relative to the total weight of the composition and the disinfectant agent being present in a content of at least 1% by weight relative to the total weight of the composition.

12. Disinfectant composition, characterized in that the disinfectant agent is a quaternary ammonium and/or a quaternary ammonium salt, chosen from alkyldimethylbenzylammonium chloride (ADBAC, BKC), the tetramethylammonium cation (TMAC), N-(3-aminopropyl)-N-dodecylpropane-1,3-diamine (diamine), N,N-didecyl-N-methylpoly(oxyethyl)ammonium propionate (Bardap26) and didecyldimethylammonium chloride (DDAC) or a mixture thereof.

The invention claimed is:

1. A method of disinfecting an inert surface by inactivating or destroying viruses on the inert surface, comprising,
   contacting the viruses with a disinfectant composition comprising a grape extract, wherein the viruses are SARS-Cov-2 coronaviruses,
   alpha coronaviruses type 229E coronavirus (HCoV-229E) or NL63 coronavirus (HCoV-NL63), or
   beta coronaviruses type HCoV-OC43 or HCoV-HKU1,
   and wherein the disinfectant composition inactivates or destroys the viruses.

2. The method according to claim 1, wherein the grape extract is an extract of seeds of the species Vitis vinifera L.

3. The method according to claim 1, wherein the inert surface is chosen from a floor, furniture, an object, or an instrument.

* * * * *